United States Patent [19]

Inoue et al.

[11] Patent Number: 5,190,866
[45] Date of Patent: Mar. 2, 1993

[54] PROCESS FOR PRODUCING ANTIBIOTIC STREPTOVARICIN

[75] Inventors: Kaname Inoue, Kawasaki; Motohide Yamazaki, Joetsu, both of Japan; Richard W. Armentrout, La Jolla, Calif.

[73] Assignee: Shin-Etsu Bio, Inc., San Diego, Calif.

[21] Appl. No.: 826,371

[22] Filed: Jan. 27, 1992

Related U.S. Application Data

[62] Division of Ser. No. 601,877, Oct. 23, 1990.

[51] Int. Cl.$^5$ .................. C12R 1/465; C12P 17/18; C12P 17/08; C07E 17/00
[52] U.S. Cl. .................. 435/119; 435/124; 435/253.5; 435/262; 435/267; 435/886; 435/803; 540/456; 540/461
[58] Field of Search ............... 435/124, 262, 267, 803, 435/253.5, 119, 886; 540/456, 461

[56] References Cited

U.S. PATENT DOCUMENTS

| | | | |
|---|---|---|---|
| 3,116,202 | 12/1963 | Dietz et al. | 435/886 |
| 3,846,400 | 11/1974 | Umezawa et al. | 435/77 |
| 4,656,143 | 4/1987 | Baker et al. | 436/529 |
| 4,659,660 | 4/1987 | Hamill et al. | 435/71 |
| 4,962,047 | 10/1990 | Place | 435/177 |

OTHER PUBLICATIONS

Reinhart et al., "Biochemistry" vol. 13 #5 pp. 861-867 (1974).
Sasaki et al., "J. Antibiotics" vol. 29 #2 pp. 147-154 (Feb. 1976).
Onodera et al., "J. Antibiotics" vol. 32 #5 pp. 545-547 (May 1979).
Wang "Annual N.Y. Academy Sciences" 431, pp. 313-321 (1983).

Primary Examiner—Herbert J. Lilling
Attorney, Agent, or Firm—McAulay Fisher Nissen Goldberg & Kiel

[57] ABSTRACT

A method for separation and recovery of polymeric beads from an antibiotic fermentation broth comprising suspending a mixture of the beads and any inherent mold from the fermentation in an aqueous solution having a specific gravity which is effective to cause the beads to form a discrete layer at or on the surface of the solution, separate and apart from the mold. The separate layer of the beads may then be easily removed from the liquid by a conventional physical methods.

1 Claim, No Drawings

PROCESS FOR PRODUCING ANTIBIOTIC STREPTOVARICIN

This is a division of application Ser. No. 07/601,877, filed Oct. 23, 1990.

BACKGROUND OF THE INVENTION

I. Field of the Invention

This invention relates to a method for the production of antibiotics by culturing microorganisms in a culture broth. More particularly, the invention concerns a method for recovering the antibiotic produced from the fermentation broth.

II. Description of the Prior Art

Methods for the production of antibiotics from microorganisms wherein a microorganism is grown in a culture medium or broth and the antibiotic produced by the microorganism is extracted from the broth are well known. Typically, the antibiotic is extracted from the fermentation broth using an organic solvent, such as, ethyl acetate, chloroform, methylene chloride, and the like. However, these organic solvents also extract other materials and components in the broth which are soluble in the solvent resulting in impurities being carried along with the extracted antibiotic. It is thus necessary to remove these impurities before final recovery and/or purification of the antibiotic. The purification processes used heretofore are complicated and expensive and result in increased costs associated with the antibiotic production process.

A typical purification process is described in U.S. Pat. No. 3,116,202 which discloses the purification of the antibiotic streptovaricin using repeated recrystallizations.

A method for increasing the production efficiency of Streptovaricin C is disclosed in U.S. patent application filed concurrently herewith and claiming priority of Japanese Patent applications 14286/1990 and 14286/1990, the contents of which are incorporated herein by reference, wherein adsorbent polymer beads are added to the fermentation broth to improve the productivity of Streptovaricin C. See also H. Wang, Annals New York Academy of Sciences, 431, 1983, pp.313-321. In these methods, the antibiotic produced from the mold essentially immediately adheres to the polymer beads and for this purpose, the mold is in close physical relationship and contact with the beads in the broth. The polymer beads are generally physically separated from the fermentation broth and adhered antibiotic product must be recovered from the beads. However, components from the broth, including the mold, are carried along with the recovered beads during the separation process resulting in impurities being carried into the resulting mixture, as well as loss of mold and difficulty in recovering the beads for reuse.

SUMMARY OF THE INVENTION

We have discovered a process for facilitating the recovery of antibiotics from fermentation broths and avoiding the expensive recovery techniques heretofore required. More particularly, we have found a method for separation and recovery of polymeric beads from an antibiotic fermentation broth which reduces the adherence of mold and impurities to the beads during the separation procedure.

The inventive process is carried out by suspending a mixture of the beads and any adherent mold and impurities in an aqueous solution having a specific gravity effective to cause the beads to form a discrete layer at or on the surface of the solution, separate and apart from the mold. Usually, of course, this would be carried out after the fermentation is complete. This may be achieved by adjusting the specific gravity of the fermentation broth itself to the effective specific gravity rang or by first separating the bead mixture from the broth and then adding an aqueous solution having a specific gravity within the effective range to the separated mixture.

The beads, with the adhered antibiotic form a layer at the surface of the liquid separate from the mold and other impurities. The beads can then be easily separated from the liquid by physical methods, e.g., filtration, skimming, washing, and the like, while leaving the mold behind. The beads can then be washed with appropriate solvents to recover the antibiotic, often with minimal recrystalization steps.

Based on this process, not only can the adsorbent polymer beads be reused, but also the impurities within the extracted antibiotic, which might come from the mold in the solvent extraction process, can be considerably decreased.

DESCRIPTION OF THE PREFERRED EMBODIMENT

In order to achieve the advantageous results of the invention, it is crucial that the specific gravity be within a range which is effective to cause the beads to separate. If the specific gravity is too low, the beads will neither separate at the surface of the solution nor from the mold. If the specific gravity is too high, the beads will not form a layer separate from the mold or at the surface of the liquid. Moreover, to the extent that the mixture of beads and mold float in the same layer, the layer will not separate at the surface of the liquid and the polymer beads cannot be recovered.

The specific gravity range which is effective to accomplish the desired result will vary depending on the particular nature of the broth, the mold and the beads. Generally, we have found that a specific gravity range of from about 1.05 to about 1.20 is preferred.

The specific gravity of the broth may be adjusted to the required value by the addition of an appropriate water soluble material, such as, an inorganic salt or an organic compound which is effective to change the specific gravity of the solution. Typical of such salts and compounds are NaCl, KCl, $Na_2SO_4$, $MgSO_4$, glycerol, glucose, sucrose, and combinations thereof. NaCl is the most preferred material because it is the most economical.

The absorbent polymer beads (resin) with the antibiotic adsorbed thereon can be recovered by physically separating the upper layer, e.g., by filtration, decanting, and the like. The separated beads can then be washed with water, dried, and then subjected to an extraction step to extract the antibiotic. Of course, any drying step would be carried out at a temperature which would not be adverse to either the beads or the antibiotic, e.g., under 40° C.

The raw antibiotics thus obtained can be subjected to conventional column-chromatographic purification directly, without recrystallization or reprecipitation.

The extracted polymer beads can be re-used by removing the organic solvent, for example, by evaporation and then boiling with water.

The following examples illustrate the invention:

EXAMPLE 1

A sterile medium (seed medium) having the following composition was prepared in a 500 ml. flask, inoculated with *Streptomyces spectabilis* ATCC27465, and incubated for 72 hours at 27° C. on a rotary shaker at 200 rpm. to produce a seed culture.

| Seed medium: | |
|---|---|
| hydrolysed casein (N-Z-amine A) | 1.25 g |
| glucose | 0.63 |
| enzyme-decomposed extract of soybean (Soytone) | 0.63 |
| $K_2HPO_4$ | 0.16 |
| $KH_2PO_4$ | 0.16 |
| distilled water | 100.00 |

A preproduction culture was prepared by inoculating a sterile medium (preproduction medium) having the following composition in a 500 ml. flask, with 2 ml of the foregoing seed culture and incubating for 48 hours at 27° C. on a rotary shaker at 200 rpm.

| Preproduction medium: | |
|---|---|
| corn dextrin | 2.0 g |
| defatted soybean meal (Kay Soy) | 1.0 |
| corn steep liquer | 1.0 |
| beer yeast | 0.25 |
| KCl | 0.3 |
| $CaCO_3$ | 0.4 |
| distilled water | 100.0 |

A production medium having the following composition was inoculated with 5ml of the thus obtained preproduction culture in a 500ml flask and incubated for 6 days at 28° C. on a rotary shaker at 200 rpm.

| Production Medium: | |
|---|---|
| glucose | 4.0 g |
| soybean meal | 4.0 |
| beer yeast | 0.25 |
| NaCl | 0.3 |
| $CaCO_3$ | 0.05 |
| $MgSO_4$ | 0.25 |
| $K_2HPO_4$ | 0.25 |
| DIAION HP-20 (polystyrene beads-50% solid) | 3.0 |
| distilled water | 100.00 |

After 6 days, the mixture of HP-20(resin) and mold was removed from the broth by filtration. The mixture (wet weight 10 g) was then dispersed in a 20% NaCl solution (specific gravity of 1.14 at 20° C.), and left standing.

The resin separated from the mold on the surface of the NaCl solution and was recovered, leaving the mold at the bottom of the solution. After washing the resin with fresh water and drying it under a vacuum at 35° C., it was extracted with 20 ml of ethyl acetate.

5 mg of crude streptovaricins containing 0.4 mg of streptovaricin C was obtained. The extracted resin could be reused as an adsorbent polymer after removing ethyl acetate under vacuum, and then boiling the resin in water.

EXAMPLE 2

Five NaCl solutions having specific gravities of 1.04, 1.07, 1.15, 1.20, and 1.22, were prepared and samples of the mixture of resin and mold obtained as in Example 1 were dispersed within each of the solutions. Clear separation was observed at specific gravities of 1.07, 1.15, and 1.20, but not at 1.04 and 1.22.

EXAMPLE 3

160 ml of the preproduction culture obtained from Example 1 was inoculated in 3 liters of sterile medium having the following composition, which was prepared in a 5 liter jar fermenter. The medium was fermented for 9 days at 27° C., 300 rpm and 1 v/v/m aeration.

| Sterile medium: | |
|---|---|
| glucose | 40.0 g/l |
| soybean meal | 40.0 |
| beer yeast | 2.5 |
| NaCl | 3.0 |
| $CaCO_3$ | 0.5 |
| $MgSO_4$ | 2.5 |
| $K_2HPO_4$ | 2.5 |
| Monosodium fumarate | 20.0 |
| defoamer (KM 75) | 2.0 |
| DIAION HP-20 (50% solid) | 100.0 |

After fermentation, about 200 g of a wet mixture of resin and mold were obtained by filtration. The mixture was then dispersed in a 15% KCl solution with a specific gravity of 1.10 at 20° C. and allowed to stand for 3 hours after which time the resin could be recovered from the surface of the solution. 0.5 g of crude Streptovaricins, which included 150 mg of Streptovaricin C, was obtained by extraction. The resin could be reused after evacuating the solvent and boiling with water.

EXAMPLE 4

A fermentation was carried out as in Example 3. The contents of the jar fermenter were then transferred to a larger container and diluted to 10 liters. NaCl was added to the container so that the specific gravity of the diluted broth was 1.14. The solution was allowed to stand for 3 hours at which time the resin was recovered from the surface of the solution.

What is claimed is:

1. In a process for the production of Streptovaricin wherein a microorganism is cultured in a broth to produce a mold of *Streptomyces spectabilis* and generate Streptovaricin in the presence of absorbent polymer beads, and the beads with Streptovaricin adhered thereto are recovered from the broth, the improvement which comprises separating the beads from the broth and treating the beads with an aqueous solution having a specific gravity effective to cause the beads to separate in a layer separate from the mold at the surface of the solution and removing the beads from the solution.

* * * * *